United States Patent [19]

Yellin et al.

[11] 4,374,836

[45] Feb. 22, 1983

[54] ANTISECRETORY HETEROCYCLIC DERIVATIVES, PROCESS FOR THEIR MANUFACTURE AND PHARMACEUTICAL COMPOSITIONS CONTAINING THEM

[75] Inventors: Tobias O. Yellin, Wallingford, Pa.; Derrick F. Jones, Tytherington, England

[73] Assignees: Imperial Chemical Industries Ltd., London, England; ICI Americas Inc., Wilmington, Del.

[21] Appl. No.: 83,479

[22] Filed: Oct. 10, 1979

[30] Foreign Application Priority Data

Oct. 16, 1978 [GB] United Kingdom ............... 40706/78

[51] Int. Cl.$^3$ .................. A61K 31/505; C07D 417/12
[52] U.S. Cl. ..................................... 424/251; 424/246; 424/249; 424/263; 544/8; 544/182; 544/320; 544/321; 546/256; 546/275; 546/276; 546/277
[58] Field of Search ....................... 544/182, 320, 321; 424/251

[56] References Cited

U.S. PATENT DOCUMENTS

| | | | |
|---|---|---|---|
| 3,932,644 | 1/1976 | Durant et al. | 424/251 |
| 4,154,834 | 5/1979 | Brown et al. | 424/251 |
| 4,185,103 | 1/1980 | Brown et al. | 544/182 |
| 4,216,318 | 8/1980 | Brown et al. | 544/310 |
| 4,218,452 | 8/1980 | Brown et al. | 424/251 |

FOREIGN PATENT DOCUMENTS 846452 3/1977 Belgium .
849810 of 0000 Belgium .
15-138 9/1980 European Pat. Off. .
1419994 1/1976 United Kingdom .

*Primary Examiner*—Donald G. Daus
*Assistant Examiner*—James H. Turnipseed
*Attorney, Agent, or Firm*—John M. Sheehan; David J. Levy

[57] ABSTRACT

The invention relates to a heterocyclic derivative of the formula:

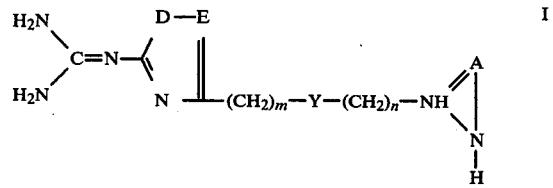

where D is O, S or NH; E is CH or when D is O or S, E is N; Y is S, O, CH$_2$, SO or a direct bond; m is 0 to 4 and n is 1 to 4, provided that when Y is S, O or SO m is 1 to 4, when Y is O or SO, n is 2 to 4; A is C$_{(3-4)}$ chain comprising at least one C and also optionally S, N, 2N or N and S, and also comprising C=O or C=S or where possible SO$_2$, the chain optionally substituted by 1 or 2 C$_{(1-6)}$ alkyl, benzyl, naphthylmethyl, 2-phenethyl, 4-phenylbutyl, pyridylmethyl, thiazolylmethyl, thienylmethyl, benzyloxy, pyridylmethoxy or phenoxymethyl radicals each optionally substituted on the aromatic ring system by 1 to 3 halogen atoms or methyl, methoxy, trifluoromethyl, dimethylamino, phenyl or phenoxy radicals; and the salts thereof.

13 Claims, No Drawings

ANTISECRETORY HETEROCYCLIC DERIVATIVES, PROCESS FOR THEIR MANUFACTURE AND PHARMACEUTICAL COMPOSITIONS CONTAINING THEM

This invention relates to heterocyclic derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit. J. Pharmac., 1966, 27, 427) and the action of histamine at this receptor is blocked (antagonized) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In U.K. Pat. No. 1,419,994 and Belgian Pat. Nos. 846,452 and 849,810 there are described histamine H-2 receptor antagonists which are imidazole, pyridine, thiazole, isothiazole or thiadiazole derivatives having a side chain to the end of which is attached, via an amino radical, a further heterocyclic ring system.

It has now been discovered that if a guanidino radical is attached to the imidazole, thiazole or thiadiazole ring carrying such a side chain there are produced compounds which are potent histamine H-2 receptor antagonists. According to the invention there is provided a heterocyclic derivative of the following formula I:

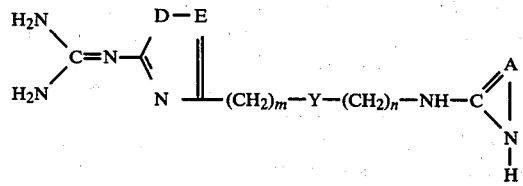

in which
D is an oxygen or sulphur atom or an NH radical;
E is a CH radical or, when D is an oxygen or sulphur atom, E may be a nitrogen atom;
Y is a sulphur or oxygen atom, a direct bond or a methylene or sulphinyl radical;
m is 0 to 4 and n is 1 to 4, provided that when Y is a sulphur or oxygen atom or a sulphinyl radical m is 1 to 4, and when Y is an oxygen atom or a sulphinyl radical n is 2 to 4;
A is a chain of 3 or 4 atoms, which chain comprises at last one carbon atom and may also comprise a sulphur atom, a nitrogen atom, two nitrogen atoms or a nitrogen atom and a sulphur atom and may contain a double bond, said chain also comprising a carbonyl or thiocarbonyl radical or where possible a sulphone radical and which chain being optionally substituted by one or two radicals selected from alkyl radicals of 1 to 6 carbon atoms and benzyl, naphthylmethyl, 2-phenethyl, 4-phenylbutyl, pyridylmethyl, thiazolyl-methyl, thienylmethyl, benzyloxy, pyridylmethoxy and phenoxymethyl radicals each optionally substituted on the aromatic ring system by one to three substituents selected from halogen atoms, such as fluoro, chloro, bromo or iodo and methyl, methoxy, trifluoromethyl, dimethylamino, phenyl and phenoxy radicals;
and the pharmaceutically-acceptable acid-addition salts thereof.

It is to be understood that in the above formula I and throughout this specification, the ring containing chain A and the guanidino radical are tautomeric systems and this invention includes all the possible tautomeric forms within its scope in terms of the compound, composition, manufacturing process and method for treatment of the invention.

A particular value for the optional substituent on the ring which includes chain A when it is an alkyl radical is a methyl radical.

The following are 6 preferred features of the heterocyclic derivatives of the formula I. When any of these 6 features is taken, either singly or in combination, with the other general or particular features of the heterocyclic derivative of the formula I listed above, there are obtained preferred sub-groups of compounds within the above definition.

1. The ring which includes chain A is one of the following formulae II to V:

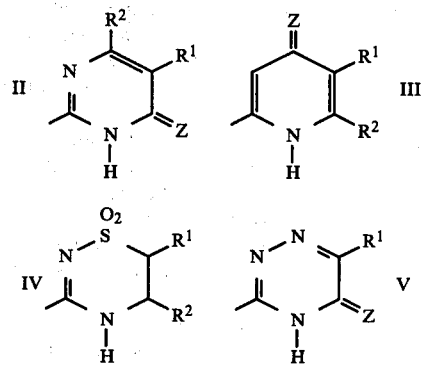

in which Z is an oxygen or sulphur atom and $R^1$ and $R^2$, which may be the same or different, are hydrogen atoms or are selected from the list of optional substituents on the chain A given above.

2. The ring which includes chain A is one of formulae II or V given above.

3. $R^2$ is a hydrogen atom and $R^1$ is a 4-chlorobenzyl, 3-methoxybenzyl or 3-pyridylmethyl radical.

4. Y is a sulphur atom or a methylene radical.

5. m is 1 and n is 2.

6. D is a sulphur atom and E is a CH radical.

Preferred compounds of the invention are those whose preparation is described in Examples 1 to 4, namely 5-(4-chlorobenzyl)-2-[2-(2-guanidinothiazol-4-ylmethylthio)ethylamino]pyrimid-4-one, 5-(4-chlorobenzyl)-2-[4-(2-guanidinothiazol-4-yl)butylamino]pyrimid-4-one, 6-(3-methyoxybenzyl)-3-[2-(2-guanidinothiazol-4-yl-methylthio)-ethylamino]-1,2,4-triazin-5-one and 6-(3-pyridylmethyl)-3-[2-(2-guanidinothiazol-4-ylmethylthio)-ethylamino]-1,2,4-tirazin-5-one. A suitable pharmaceutically-acceptable acid-addition salt of the heterocyclic derivative of the formula I is, for example, a salt formed with hydrochloric, hydrobromic, phosphoric, sulphuric, acetic, citric or maleic acid.

The heterocyclic derivative of the invention may be manufactured by methods known in themselves for the manufacture of chemically analogous compounds. Thus the following process, A, D, E, Y, m and n having the meanings stated above, is provided as a further feature of the invention.

The process of the invention is characterized by reaction of compound of the following formula VI:

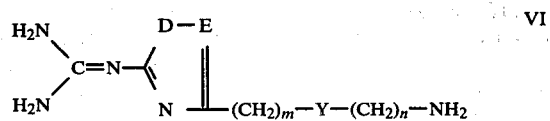

with a compound of the following formula VII:

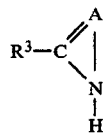

in which $R^3$ is a displaceable radical. $R^3$ may, for example, be a halogen atom, for example a chlorine or bromine atom, or an alkylthio radical of 1 to 6 carbon atoms, for example a methylthio radical. The reaction may be conducted in the absence of a diluent or solvent at an elevated temperature, for example at a temperature of 100° to 150° C., or it may be conducted in a diluent or solvent, such as pyridine, at the boiling point of the diluent or solvent.

When an acid-addition salt of the compound of the formula I is required, the compound of the formula I in the free base form is reacted with an acid which affords a pharmaceutically-acceptable anion.

The compound of the formula VI may, for example, be prepared as described in Belgian Pat. Nos. 866,155 and 866,156 and in copending U.S. Patent applications Ser. Nos. 36,360 and 36,361, both filed on May 7, 1979, the Belgian Patents and U.S. Patent applications all being assigned to the assignee of the present invention.

As noted above, the heterocyclic derivative of the invention is a histamine H-2 antagonist, inhibits the secretion of gastric acid in warm-blooded animals such as man and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml) containing oxygenated (95% $O_2$; 5% $CO_2$) Krebs-Hanseleit buffer (pH 7.4). The tissue is allowed to stabilize over 1 hour during which time it is washed 2–4 times. Individual contractions are recorded with a force-displacement transducer through a strain gauge couple, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu$M.

The histamine-stimulated cyclic AMP test is carried out as described by Scholes et al., *Agents and Actions*, 1976, 6, 677–682.

The inhibition of the secretion of gastric acid may be demonstrated in standard tests, for example by the ability of the compound of the formula I, when dosed intravenously, intragastrically or orally, to inhibit the secretion of gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (8–12 kg) having chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mole/kg/hour of histamine or 2 $\mu$g/kg/hour pentagastrin) in saline (15 ml/hour) is begun. Gastric acid samples are collected every 15 minutes. The volume of each sample is measured and a 1 ml aliquot is titrated to neutrality with 0.1 N NaOH to determine acid concentration. When a plateau of secretion is reached, (1–2 hours) the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml of 0.5% w/v hydroxypropyl methylcellulose and 0.1% w/v 'Tween' 80 in water ('Tween' is a Trademark), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test and/or the histamine stimulated cyclic AMP test are predictive of activity in the dog test. No overt toxicity or side effects were noted during the dog tests.

Some of the heterocyclic derivatives of the invention, and in particular those in which the ring which contains chain A is of the formula II or V, are also histamine H-1 antagonists and this effect may be demonstrated on standard test systems such as the guinea pig ileum. A compound having such a property is useful for the treatment of conditions involving an immune reaction, for example allergic conditions.

Many of the actions of histamine are mediated by histamine H-1 and H-2 receptors and a compound combining both H-1 and H-2 antagonist properties is useful for the treatment of certain states, for example inflammation and the inhibition of the effects of histamine on blood pressure and the prevention and treatment of anaphylactic shock.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purpose it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the heterocyclic derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical compositon of the invention for topical administration may also contain, in addition to the heterocyclic derivative, one or more classical antihistamines (histamine H-1 antagonists), for example mepyramine or diphenhydramine and/or one or more steroidal anti-inflammatory agents, for example fluocinolone or triamcinolone.

A topical formulation may contain about 1 to 10% w/w of the heterocyclic derivative of the invention. A preferred pharmaceutical composition of the invention is one suitable for oral administration in unit dosage form, for example a tablet or capsule which contains from about 10 mg to 500 mg of the heterocyclic derivative, or one suitable for intravenous, subcutaneous or intramuscular injection, for example a sterile injectable containing from about 0.1% to 10% w/w of the heterocyclic derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the heterocyclic derivative of the present invention relative to cimetidine. Thus each patient will receive an oral dose of from about 20 mg to 1500 mg and preferably from about 50 mg to 500 mg of heterocyclic derivative or an intravenous, subcutaneous or intramuscular dose of from about 2.5 mg to 150 mg preferably from about 10 mg to 50 mg of the heterocyclic derivative, the composition being administered 2 to 4 times per day. The rectal dose will be approximately the same as the oral dose. The composition may be administered less frequently when it contains an amount of heterocyclic derivative which is a multiple of the amount which is effective when given 2 to 4 times per day. When employing the H-1 or H-1/H-2 antagonist properties of the pharmaceutical compositon of the invention, the same dose levels as are described above may be used.

The invention is illustrated, but not limited, by the following Examples.

EXAMPLE 1

A mixture of 2-guanidino-4-[(2-aminoethyl)thiomethyl]thiazole (1.06 g) and 5-(4-chlorobenzyl)-2-methyl thiopyrimid-4-one (1.23 g) was heated at 115° C. in an oil bath for 16 hours. The product was purified by preparative thin layer chromatography (TLC) using chloroform/methanol/ammonia (s.g. 0.88) 84:15:1 v/v/v as developing solvent. There was thus obtained 0.0967 g of 5-(4-chlorobenzyl)-2-[2-(2-guanidinothiazol-4-ylmethylthio)ethylamino]pyrimid-4-one, m.p. 205°–207° C. on recrystallization from methanol.

EXAMPLE 2

A mixture of 2-guanidino-4-(4-aminobutyl)thiazole (1.0 g) and 5-(4-chlorobenzyl)-2-methylthiopyrimid-4-one (1.2 g) was heated at 115° C. in an oil bath for 16 hours. The product was purified by preparative TLC using chloroform/methanol/ammonia (s.g. 0.88) 80:20:1 v/v/v as developing solvent. There was thus obtained 0.026 g of 5-(4-chlorobenzyl)-2-[4-(2-guanidinothiazol-4-yl)butylamino]pyrimid-4-one, m.p. 200°–205° C. on recrystallization from methanol.

EXAMPLE 3

A mixture of 3-methylthio-6-(3-methoxybenzyl)-1,2,4-triazin-5-one (1.0 g) and 2-guanidino-4-[(2-aminoethyl)thiomethyl]thiazole (0.924 g) was heated at 135° C. for 3 hours. The residue was dissolved in dimethyl formamide (20 ml) and the solution was allowed to stand at room temperature for 8 days. A yellow brown solid precipitated out of solution, and this was filtered off and dried in air, then purified using pressure assisted short bed column chromatography (Kieselgel 60) with chloroform/methanol/ammonia (s.g. 0.880) 8:2:0.3 v/v/v as eluant, to give 6-(3-methoxybenzyl)-3-[2-(2-guanidinothiazol-4-yl-methylthio)ethylamino]-1,2,4-triazin-5-one (0.1 g). The n.m.r. spectrum of the product in $d_4$ acetic acid using tetramethylsilane as an internal standard ($\delta = 0$) had the following resonances ($\delta$): 2.8 (2H, multiplet); 3.5 (2H, multiplet); 3.75 (5H, singlet); 3.9 (2H, singlet); 6.8–6.9 (4H, multiplet); 7.2 (1H, broad doublet).

EXAMPLE 4

A mixture of 3-methylthio-6-(3-pyridylmethyl)-1,2,4-triazin-5-one (0.23 g) and 2-guanidino-4-[(2-aminoethyl)thiomethyl]thiazole (0.23 g) was heated at 140° C. for 2 hours and then allowed to cool to room temperature. The black solid mass was triturated with a mixture of methanol (10 ml) and dimethylformamide (2 ml) and the resulting pale brown solid was filtered off. This was purified by preparative TLC using Merck Kieselgel GF 254 2 mm preparative plates in chloroform/methanol-/ammonia (s.g. 0.880) 8:2:0.3 v/v/v as eluant to give 6-(3-pyridylmethyl)-3-[2-(2-guanidinothiazol-4-ylmethylthio)-ethylamino]-1,2,4-triazin-5-one (0.08 g). The n.m.r. spectrum of the product in d$_6$ dimethyl sulphoxide using tetramethylsilane as an internal standard ($\delta=0$) had the following resonances: 2.7 (2H, triplet); 3.4 (2H, broad multiplet); 3.6 (2H, sharp singlet); 3.8–4.1 (8H, broad multiplet—contains H$_2$O); 6.6 (1H, sharp singlet); 6.9 (4H, broad singlet); 7.3 (1H, multiplet); 7.7 (1H, double triplet); 8.5 (2H, multiplet).

EXAMPLE 5

A pharmaceutical tablet composition containing a derivative of formula I may be prepared by combining, mixing and compressing the following ingredients into slugs:

| | |
|---|---|
| 5-(4-chlorobenzyl)-2-[2-(2-guanidinothiazol-4-ylmethylthio)-ethylamino]pyrimid-4-one | 100 g |
| Starch | 102 g |
| Powdered Lactose | 102 g |
| Talc | 26 g |
| Total | 330 g |

The slugs should then be ground to form granules that will pass through a 14 to 16 mesh screen. The granules may then be recompressed into about 1000 tablets using a suitable compression mold to form tablets.

What is claimed is:

1. A heterocyclic derivative of the following formula (I):

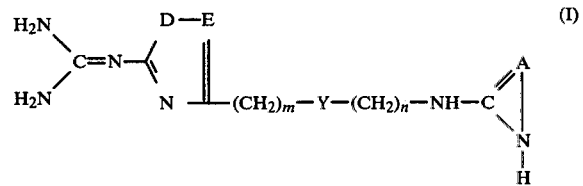

in which
D is an oxygen or sulphur atom or an NH radical;
E is a CH radical or, when D is an oxygen or sulphur atom, E is a nitrogen atom;
Y is a sulphur or oxygen atom, a direct bond or a methylene or sulphinyl radical;
m is 0 to 4 and n is 1 to 4, provided that when Y is a sulphur or oxygen atom or a sulphinyl radical m is 1 to 4, and when Y is an oxygen atom or a sulphinyl radical, n is 2 to 4; and
the ring which includes chain A is of the following formula (II):

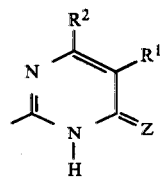

in which
Z is an oxygen or sulphur atom; and
$R^1$ and $R^2$, which may be the same or different, are hydrogen atoms or are radicals selected from alkyl radicals of 1 to 6 carbon atoms, and benzyl, naphthylmethyl, 2-phenethyl, 4-phenylbutyl, pyridylmethyl, thiazolylmethyl, thienylmethyl, benzyloxy, pyridylmethoxy and phenoxymethyl radicals each optionally substituted on the aromatic ring system by one to three substituents selected from halogen atoms and methyl, methoxy, trifluromethyl, dimethylamino, phenyl and phenoxy radicals; and the pharmaceutically-acceptable acid-addition salts thereof.

2. The heterocyclic derivative as claimed in claim 1 wherein Z is an oxygen atom.

3. The heterocyclic derivative as claimed in claim 1 wherein $R^1$ is a 4-chlorobenzyl,3-methoxybenzyl or 3-pyridylmethyl radical and $R^2$ is a hydrogen atom.

4. The heterocyclic derivative as claimed in claim 1 wherein $R^1$ is a pyridylmethyl radical and $R^2$ is a hydrogen atom.

5. The heterocyclic derivative as claimed in claim 1 wherein Y is a sulphur atom or methylene radical.

6. The heterocyclic derivative as claimed in claim 5 wherein m is 1 and n is 2.

7. The heterocyclic derivative as claimed in claim 1 wherein D is a sulphur atom and E is a CH radical or a nitrogen atom.

8. The heterocyclic derivative as claimed in claim 1, wherein said derivative is 5-(4-chlorobenzyl)-2-[2-(2-guanidinothiazol-4 -ylmethylthio)-ethylamino]pyrimid-4-one.

9. A compound selected from 5-(4-chlorobenzyl)-2-[2-(2-guanidinothiazol-4-ylmethylthio)ethylamino]-pyrimid-4-one and 5-(4-chlorobenzyl)-2-[4-(2-guanidinothiazol-4-yl)-butylamino]pyrimid-4-one and the pharmaceutically-acceptable acid-addition salts thereof.

10. A compound of the formula

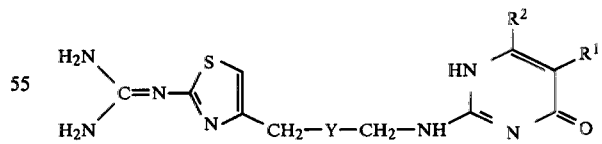

in which Y is sulfur or methylene; $R^2$ is hydrogen or lower alkyl of 1 to 6 carbon atoms, $R^1$ is selected from the group consisting of pyridylmethyl, thiazolylmethyl, thienylmethyl, benzyl, naphthylmethyl, benzyloxy, pyridylmethoxy, and phenoxymethyl radicals, each optionally substituted on the aromatic ring system by one to three substituents selected from halogen atoms, and methyl, methoxy, trifluromethyl, dimethylamino, phenyl and phenoxy radicals; and the pharmaceutically acceptable acid-addition salts thereof.

11. A compound of the formula

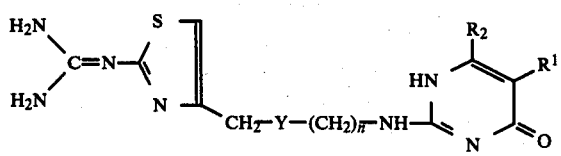

in which Y is sulfur or methylene; n is 1 to 4; $R^2$ is hydrogen or lower alkyl of 1 to 6 carbon atoms; $R^1$ is selected from the group consisting of pyridylmethyl, thiazolylmethyl, thienylmethyl, benzyl, naphthylmethyl, benzyloxy, pyridylmethoxy, and phenoxymethyl radicals, each optionally substituted on the aromatic ring system by one to three substituents selected from halogen atoms, and methyl, methoxy, trifluromethyl, dimethylamino, phenyl and phenoxy radicals; and the pharmaceutically acceptable acid-addition salts thereof.

12. A pharmaceutical composition comprising a heterocyclic derivative as claimed in claim 1 in association with a non-toxic pharmaceutically-acceptable diluent or carrier.

13. A method of inhibiting gastric acid secretion in a living animal comprising administering to the animal a therapeutically effective amount of the composition of claim 12.

* * * * *